United States Patent
Powers et al.

(10) Patent No.: US 10,438,687 B1
(45) Date of Patent: Oct. 8, 2019

(54) DYNAMIC EVALUATION OF POLYGENIC MODELS BASED ON GENETIC LOCI FOR WHICH INPUT IS RECEIVED

(71) Applicant: Helix OpCo, LLC, San Carlos, CA (US)

(72) Inventors: Rani K. Powers, Broomfield, CO (US); Ryan P. Trunck, Denver, CO (US); Christopher M. Glode, Denver, CO (US)

(73) Assignee: Helix OpCo, LLC, San Carlos, CA (US)

( * ) Notice: Subject to any disclaimer, the term of this patent is extended or adjusted under 35 U.S.C. 154(b) by 0 days.

(21) Appl. No.: 16/033,955

(22) Filed: Jul. 12, 2018

(51) Int. Cl.
 *G16B 10/00* (2019.01)
 *G16B 40/00* (2019.01)
 *G16B 30/00* (2019.01)

(52) U.S. Cl.
 CPC ............ *G16B 10/00* (2019.02); *G16B 30/00* (2019.02); *G16B 40/00* (2019.02)

(58) Field of Classification Search
 None
 See application file for complete search history.

(56) References Cited

U.S. PATENT DOCUMENTS 9,922,285 B1    3/2018   Glode et al.

OTHER PUBLICATIONS

Ritchie et al. Methods of integrating data to uncover genotype-phenotype interactions Nature Reviews Genetics vol. 16, pp. 85-97 (Year: 2015).*
Kell Genotype-phenotype mapping: genes as computer programs Trends in Genetics vol. 18, pp. 555-559 (Year: 2002).*
Diane L. Byers PhD et al; Adaptation and Phenotypic Variance; Scitable by nature education; Apr. 19, 2018.
Genome Browser FAQ; https://genome.ucsc.edu/FAQ/FAQformat.html; May 21, 2018.
IGSR: The International Genome Sample Resource; http://www.internationalgenome.org/wiki/Analysis/vcf4.0; May 21, 2018.
Luigi Palla et al; A Fast Method that Uses Polygenic Scores to Estimate the Variance Explained by Genome-wide Marker Panels and the Proportino of Variants Affecting a Trait; The American Journal of Human Genetics 97, 250-259, Aug. 6, 2015.
Naomi R. Wray PhD et al; Estimating Trait Heritability; Scitable by nature education; Apr. 19, 2018.
Nicholas A. Furlotte et al.; 23andMe; White Paper 23-12; Estimating Complex Phenotype Prevalence Using Predictive Models; Sep. 25, 2015.
Rasmus Nielsen et al; Genotype and SNP calling from next-generation sequencing data; Nature Reviews Genetics vol. 12, pp. 443-451.
The Minitab Blog; Regression Analysis: How Do I Interpret R-squared and Assess the Goodness-of-Fit?Apr. 19, 2018.
U.S. Appl. No. 15/689,596, Glode et al, filed Aug. 29, 2017.
Wikipedia; Coeffecient of dertermination; Apr. 19, 2018.

* cited by examiner

*Primary Examiner* — John S Brusca
(74) *Attorney, Agent, or Firm* — Duft & Bornsen, PC

(57) ABSTRACT

Systems and methods are provided for evaluating polygenic models. One embodiment is a system that includes a memory storing a polygenic model that uses genetic variants which occupy predetermined genetic loci as inputs, and makes predictions for individuals based on the inputs. The system also includes an interface that receives an indication of known genetic variants exhibited by an individual, and a controller. The controller operates the model to make a prediction for the individual, determines that the indication does not provide known genetic variants for a subset of the predetermined genetic loci, and evaluates a performance of the prediction of the model based on the subset of the predetermined genetic loci that have not been provided known genetic variants.

20 Claims, 11 Drawing Sheets

FIG. 4

| NAME | GENETIC LOCUS/LOCI | GENETIC VARIANT | GENOTYPE QUALITY | IMPUTED? | OMITTED? | REASON FOR OMISSION |
|---|---|---|---|---|---|---|
| SNP 645 | CHR. 7, PSN. 1760 | A | 10 | Y | N | N/A |
| SNP 1324 | CHR. 5, PSN. 2235 | G | 28 | N | N | N/A |
| SNP 1261 | CHR. 13, PSN. 1921 | T | 59 | N | N | N/A |
| SEQUENCE 15 | CHR.23, PSN. 3519-3524 | AATGCA | 5 | N | N | N/A |
| SNP 3550 | CHR. 7, PSN 590 | UNREPORTED | N/A | N/A | Y | PERMISSION DENIED |

DYNAMIC EVALUATION OF POLYGENIC MODELS BASED ON GENETIC LOCI FOR WHICH INPUT IS RECEIVED

FIELD

The disclosure relates to the field of genomics, and in particular, to polygenic models.

BACKGROUND

The genes of individuals code for a variety of proteins. The expression of a gene in messenger Ribonucleic Acid (mRNA) and protein contributes to a variety of phenotypic traits (i.e., observable traits such as eye color, hair color, etc.) as well as other traits. If a variant occurs in a specific gene, that variation is reflected in mRNA and protein, which can result in a different phenotype. Genetic factors therefore play a major role in a variety of phenotypic traits. For example, normal variations (polymorphisms) in two genes, EDAR and FGFR2, have been associated with differences in hair thickness. Each variation in the nucleotides found in a gene (or the nucleotides that regulate expression of that gene) may be considered a genetic variant.

While biological inheritance of physical traits has been studied for decades, associating specific phenotypes with specific genetic variants or combinations thereof remains a complicated process. The human genome itself occupies approximately eighty Gigabytes (GB) of data. Furthermore, there are estimated to be roughly ten million Single Nucleotide Polymorphisms (SNPs) within the genome. Large stretches of the genome include non-coding regions (e.g., introns) as well as coding regions (e.g., exons), and the non-coding regions may regulate how one or more coding regions are expressed. Thus, even variations in non-coding regions may have an impact on phenotype, and false positives may occur when associating a genetic variant with a specific phenotype. Hence, the process of correlating specific genetic variants with specific traits (e.g., specific phenotypes) can be fiendishly complex.

Further increasing the complexity of the process, it is not possible to identify many traits of an individual without studying the individual closely, and some traits may be hard to precisely quantify (e.g., hair curl, personality, etc.). Some traits may be hard to identify based on the information currently known about the individual. For example, an individual who has constant headaches may be suffering from high blood pressure, high stress, allergies, or other conditions. Without more information, it would be impossible to determine which genetic variants exist within that individual that are correlated with (and/or contribute to) the reported traits or symptoms.

Mathematical models have been built which attempt to predict the traits of an individual based on the genetic sequence of an individual. However, the accuracy, speed, and complexity of such models varies wildly. Even models that are accurate for the general population may produce less accurate predictions when applied to members of certain subpopulations, due to genetic variation or other factors which may not have been captured in the original model. Furthermore, individuals may be unwilling to share the amount and type of genetic data desired as input for the models discussed above.

Hence, those who seek to identify generalizable and robust relationships between traits of individuals and the genetic variants found in those individuals continue to seek out enhanced methods for achieving these goals.

SUMMARY

Embodiments described herein evaluate the performance of polygenic models that make predictions about an individual based on the genetic variants determined to exist within that individual. Because the amount of genetic content provided by each individual may vary (e.g., based on privacy concerns or differences in what portions of the individual's genome have been genotyped or sequenced), embodiments described herein dynamically determine the performance of a prediction made by a polygenic model based on the particular combination of genetic variants that were provided as input to the model. For example, the performance of a polygenic model may be determined for each prediction based on the number of genetic loci for which genetic variants have been provided as input and/or predetermined weights for each genetic variant in the provided input combination. The systems and methods described herein may provide personalized feedback to users in the form of a confidence score that is tailored to each prediction made about the user. Such confidence scores may indicate the estimated accuracy of predictions made for the user by the polygenic model, a Proportion of Variance Explained (PVE) for the prediction made by polygenic model, etc.

One embodiment is a system that includes a memory storing a polygenic model that uses genetic variants which occupy predetermined genetic loci as inputs, and makes predictions for individuals based on the inputs. The system also includes an interface that receives an indication of known genetic variants exhibited by an individual, and a controller. The controller operates the model to make a prediction for the individual, determines that the indication does not provide known genetic variants for a subset of the predetermined genetic loci, and evaluates a performance of the prediction of the model based on the subset of the predetermined genetic loci that have not been provided known genetic variants.

A further embodiment is a method. The method includes selecting a polygenic model that uses genetic variants which occupy predetermined genetic loci as inputs, receiving an indication of known genetic variants exhibited by an individual, operating the model to make a prediction for the individual, determining that the indication does not provide known genetic variants for a subset of the predetermined genetic loci, and evaluating a performance of the prediction of the model based on the subset of the predetermined genetic loci that have not been provided known genetic variants.

Yet another embodiment is a non-transitory computer readable medium embodying programmed instructions which, when executed by a processor, are operable for performing a method. The method includes selecting a polygenic model that uses genetic variants which occupy predetermined genetic loci as inputs, receiving an indication of known genetic variants exhibited by an individual, operating the model to make a prediction for the individual, determining that the indication does not provide known genetic variants for a subset of the predetermined genetic loci, and evaluating a performance of the prediction of the model based on the subset of the predetermined genetic loci that have not been provided known genetic variants.

Other illustrative embodiments (e.g., methods and computer-readable media relating to the foregoing embodiments) may be described below. The features, functions, and advantages that have been discussed can be achieved independently in various embodiments or may be combined in yet other embodiments further details of which can be seen with reference to the following description and drawings.

DESCRIPTION OF THE DRAWINGS

Some embodiments of the present disclosure are now described, by way of example only, and with reference to the accompanying drawings. The same reference number represents the same element or the same type of element on all drawings.

FIG. 4 is a table illustrating known genetic variants for an individual which are provided as input to a polygenic model in an illustrative embodiment.

DESCRIPTION

The figures and the following description depict specific illustrative embodiments of the disclosure. It will thus be appreciated that those skilled in the art will be able to devise various arrangements that, although not explicitly described or shown herein, embody the principles of the disclosure and are included within the scope of the disclosure. Furthermore, any examples described herein are intended to aid in understanding the principles of the disclosure, and are to be construed as being without limitation to such specifically recited examples and conditions. As a result, the disclosure is not limited to the specific embodiments or examples described below, but by the claims and their equivalents.

Figure 1:
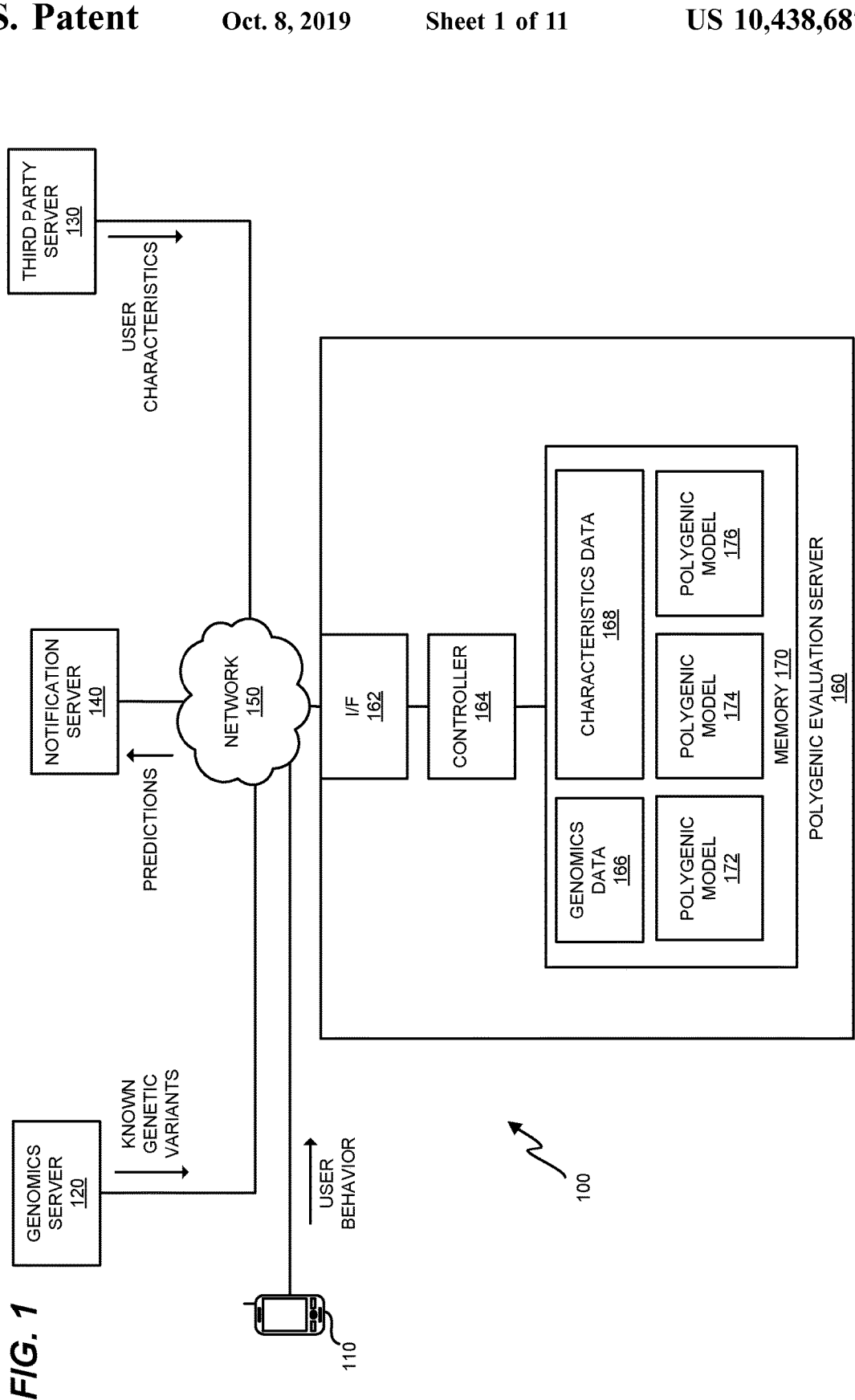
FIG. 1 is a block diagram of a polygenic evaluation system in an illustrative embodiment.

FIG. 1 is a block diagram of a polygenic evaluation system 100 in an illustrative embodiment. Polygenic evaluation system 100 comprises any system, device, or component which evaluates the performance of predictions that are made about an individual based on genetic variants exhibited by that individual. Specifically, polygenic evaluation system 100 evaluates predictions from polygenic models that use the genetic variants found within an individual as input.

In this embodiment, polygenic evaluation system 100 includes user device 110 (e.g., a computer, cellular phone, or tablet of a user), genomics server 120, and one or more third party servers 130. These entities provide input via network 150 (e.g., the Internet, a combination of small networks, etc.) to polygenic evaluation server 160.

Polygenic evaluation server 160 receives information from user device 110, genomics server 120, and/or third party server 130. For example, polygenic evaluation server 160 may receive login information, commands, and user feedback from user device 110, may receive records (e.g., Variant Call Format (VCF) files indicating genetic variants exhibited by an individual) from genomics server 120, and may already store information describing characteristics or preferences of an individual. In further embodiments, polygenic evaluation server 160 may receive characteristic information from user device 110. In one embodiment, information describing characteristics or preferences of an individual are also provided by one or more third party servers 130.

Records from genomics server 120 indicate the genetic variants exhibited by a specific individual. Polygenic evaluation server 160 uses these records as input to polygenic models 172-176, which generate predictions about that individual. Polygenic models 172-176 may comprise machine learning models (e.g., neural networks, genetic algorithms, other stochastic or deterministic models, etc.) that have already been trained based on a vetted set of training data, or may comprise other predictive models. While only three polygenic models are illustrated in FIG. 1, any suitable number of models may be utilized by polygenic evaluation server 160. In addition to operating polygenic models 172-176 to make predictions, polygenic evaluation server 160 also determines the quality of these predictions, based on the number and/or type of genetic variants used as input to the models.

In this embodiment, polygenic evaluation server 160 includes interface (I/F) 162 and controller 164. I/F 162 receives and transmits data via network 150, and may comprise any suitable component for transmitting data, such as an Ethernet port, a wireless transceiver compatible with IEEE 802.11 protocols, etc. Controller 164 manages the operations of polygenic evaluation server 160 by coordinating and evaluating the process of prediction. Controller 164 may be implemented, for example, as custom circuitry, as a hardware processor executing programmed instructions, or some combination thereof.

Controller 164 stores genomics data 166 in memory 170 based on input from genomics server 120 and/or user device 110. Memory 170 may comprise any suitable non-transitory computer readable storage medium, such as a solid state memory, hard disk, etc. Genomics data 166 may include records indicating the genomics of a population (e.g., millions of individuals), on an individual-by-individual basis. The records may describe genetic variants previously identified in specific individuals within the population. For example, each record in genomics data 166 may indicate known genetic variants found within a specific individual, and different records may correspond with different individuals. In a further embodiment, a record in genomics data may report the existence (or non-existence) of a specific genetic variant for a large number of specified individuals. As used herein, the term "genetic variant" refers to a variation of an individual gene (e.g., alleles, Single Nucleotide Polymorphisms (SNPs), etc.), as well as epigenetic variations, variations in nucleotides that regulate gene expression or gene activity, etc.

Controller 164 may also store characteristics data 168 in memory 170 based on input from third party server 130 and/or user device 110. As used herein, the "characteristics" of an individual include phenotypes exhibited by an individual, such as hair color, eye color, height, etc. Characteristics also include behaviors of the individual such as fitness patterns, dietary habits, travel patterns, social networking behaviors and preferences (e.g. "Likes" of a sports team or political party), etc. Characteristics may even include the ancestry of an individual, the sex of an individual, the "digital footprint" of an individual (e.g., interactions with others on a social network, financial transactions performed by the individual), a history of medical treatment for the individual, etc. Polygenic models 172-176 may utilize such characteristics as additional inputs for the prediction process.

With the above description provided of "characteristics," it will be understood that characteristics data 168 may comprise one or more records that indicate characteristics of specific individuals. For example, records may comprise Electronic Health Records (EHRs) or may report a pulse rate of a user over time during a workout. The data within the records therefore may indicate a characteristic such as a level of cardiovascular health. In other examples, the records may indicate a pattern of purchases of an individual that suggest that the individual has a specific characteristic, such as nearsightedness, acid reflux, or a desire for travel.

Controller 164 utilizes genomics data 166, optionally in combination with characteristics data 168, as inputs to one or more polygenic models 172-176, and makes predictions regarding individuals based on the output of these models. For example, a prediction may attempt to assign a characteristic to an individual (e.g., brown hair, tall, etc.). Controller 164 also evaluates the performance of predictions made by each model, as will be described below with regard to FIG. 2, and may generate reports that evaluate the performance (e.g., accuracy or other metrics) of each prediction. These reports may be provided to notification server 140 for distribution via I/F 162 for distribution to user device 110.

Illustrative details of the operation of polygenic evaluation system 100 will be discussed with regard to FIG. 2. Assume, for this embodiment, that a user has accessed polygenic evaluation system 100 in order to make personalized predictions for an individual, based on the genetic variants exhibited by that individual.

Figure 2:
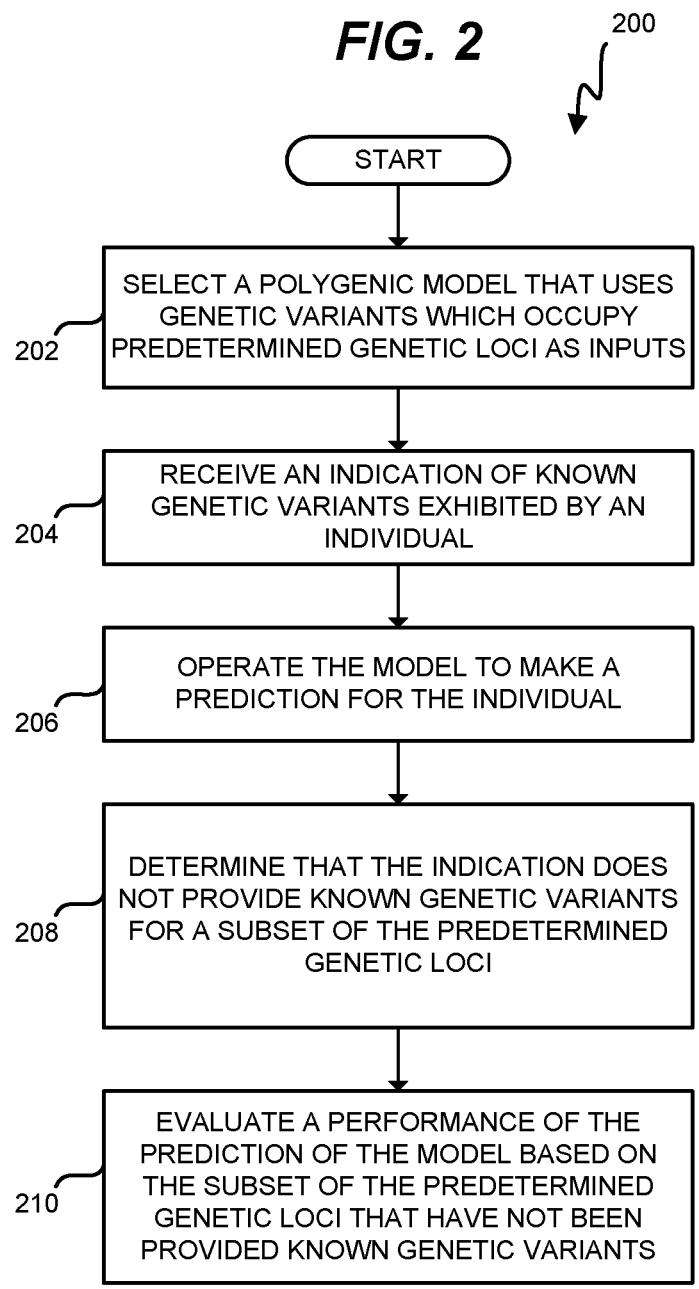
FIG. 2 is a flowchart illustrating a method for operating a polygenic evaluation system in an illustrative embodiment.

FIG. 2 is a flowchart illustrating a method 200 for operating a polygenic evaluation system 100 in an illustrative embodiment. The steps of method 200 are described with reference to polygenic evaluation system 100 of FIG. 1, but those skilled in the art will appreciate that method 200 may be performed in other systems. The steps of the flowcharts described herein are not all inclusive and may include other steps not shown. The steps described herein may also be performed in an alternative order.

In step 202, controller 164 selects a polygenic model 172. A polygenic model will make a prediction (e.g., predicting the existence or nonexistence of a characteristic, a set of characteristics, or a genotype) for the individual. For each of multiple locations on chromosomes that have been measured/quantified, a polygenic model may consider the existence (or nonexistence) of specific genetic variants when making predictions. For example, a polygenic model may generate one output in response to one measured genetic variant at a location, but may generate a different output in response to detecting a different measured genetic variant at the same location.

Each polygenic model expects to receive information describing genetic variants for an individual that occupy predetermined genetic loci (e.g., locations on a chromosome, locations within the genome as a whole, a range of locations on a chromosome, etc.). The predetermined genetic loci may vary between polygenic models. For example, polygenic model 172 may expect information describing three Single Nucleotide Polymorphisms (SNPs) at three separate predetermined genetic loci on a chromosome, while polygenic model 174 may expect four genetic sequences that each occupy a range of predetermined genetic loci on a different chromosome. Polygenic models 172-176 may expect input describing genetic variants found at a wide range of predetermined genetic loci (e.g., hundreds or tens of thousands of genetic loci). However, a polygenic model remains sufficiently robust that it may generate predictions even when a genetic variant is not received as input for each and every of the predetermined genetic loci used as input (i.e., in circumstances when not all genetic loci used as input by the polygenic model have been measured or reported to the model).

In further embodiments, the selection process for a polygenic model may also consider one or more characteristics of the individual as input. For example, certain polygenic models for predicting a predisposition towards lung cancer may be more accurate for smokers than for non-smokers. By accounting for the characteristics of an individual during the selection process (e.g., in addition to the genetic sequence of the individual), an ideal polygenic model may be selected.

Controller 164 also receives an indication (e.g., one or more records) of known genetic variants exhibited by the individual in step 204. The indication may comprise, for example, a list of known genetic variants, along with the genetic loci occupied by those genetic variants. Although the indication describes known genetic variants for the individual, it need not include all genetic variants desired by the selected model. Polygenic model 172 remains capable of making predictions with this limited amount of information, but the quality of predictions made by polygenic model 172 will be lower than expected by default. The degree to which prediction quality is degraded is not yet known.

Controller 164 proceeds to operate polygenic model 172 to make a prediction for the individual in step 206. For example, if polygenic model 172 is a neural network (e.g., a convolutional network, deep neural network, a recurrent neural network, etc.), controller 164 may apply the known genetic variants as input to the neural network and determine an output. In a further example where polygenic model 172 is an equation, controller 164 may utilize the existence or nonexistence of known genetic variants to selectively include or omit (or set to null or zero) segments of the equation that correspond with predetermined genetic loci for which no known genetic variants have been provided. The polygenic model yields a prediction, but the quality of the prediction is not yet known. To address this, controller 164 takes steps to determine how the missing inputs to polygenic model 172 have impacted the quality of the prediction.

In step 208, controller 164 determines that the indication does not provide known genetic variants for a subset of the predetermined genetic loci. For example, controller 164 may determine that while known genetic variants have been provided for sixteen out of twenty-two predetermined genetic loci desired as input for polygenic model 172, known genetic variants have not been provided for six remaining predetermined genetic loci used by polygenic model 172 as input. Controller 164 may further store information indicating the specific predetermined genetic loci for which no known genetic variants have been provided.

In step 210, controller 164 evaluates a performance of the prediction of the polygenic model 172 based on the subset of the predetermined genetic loci that have not been provided known genetic variants. The performance is therefore evaluated for the specific prediction made for the individual. Controller 164 may determine performance as an estimated accuracy of the prediction, an estimated Proportion of Variance Explained (PVE) of the prediction, etc. Specific techniques which may be used for the evaluation of performance are provided below.

Controller 164 may further generate and transmit a report to notification server 140 for provisioning to the user. Notification server 140 receives reports from polygenic evaluation server 160 via network 150, and transmits the reports to genomics server 120, third party server 130, and/or one or more user devices 110 of users. In this manner, reports are provided to those who have an interest in the predictive assignments performed at polygenic evaluation server 160. Notification server 140 may further anonymize personal data for the individual within the reports if desired, in order to ensure that privacy is maintained. For example, if a report is provided to a third party, the report may be anonymized to protect the privacy of the individual. Reports may also be utilized to develop applications pertaining to polygenic evaluation server 160, and/or for internal research.

Method 200 provides a substantial advantage over prior techniques in that it is capable of determining the performance of specific predictions made by polygenic models, and is capable of determining this performance based on the number and/or type of genetic loci for which known genetic variants have been provided. In this manner, the estimated performance of a polygenic model may vary on a prediction-by-prediction basis, based on what combination of genetic data is used as input. This ability to dynamically determine accuracy and/or other performance metrics based on the combination of genetic data submitted is particularly valuable because many individuals may not be able (or willing) to provide all genetic data requested as input to the models. For example, even individuals who have had their entire genome sequenced may have portions of their genome for which no accurate data exists (e.g., owing to insufficient sequencing data, conflicting sequencing data, chemical anomalies that occur during sequencing, etc.).

Figure 3:
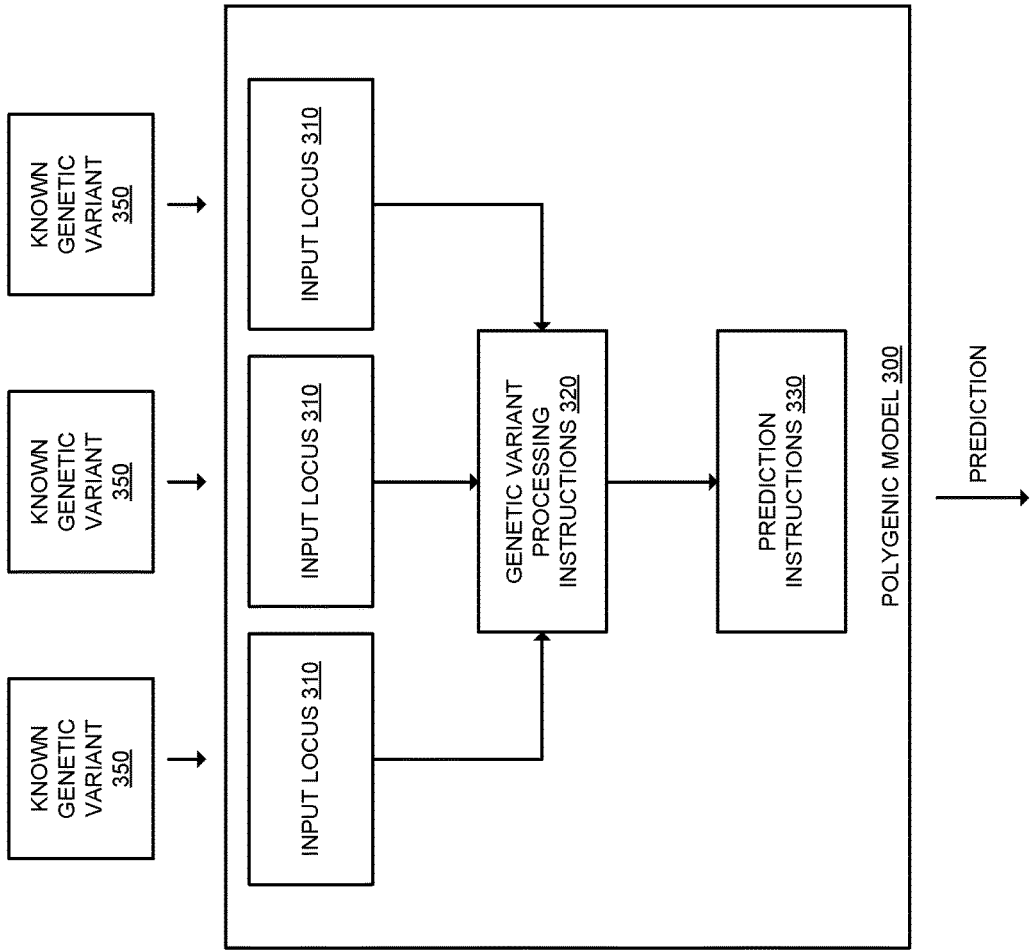
FIG. 3 is a block diagram of a polygenic model that receives input defining known genetic variants corresponding with predetermined genetic loci in an illustrative embodiment.

FIG. 3 is a block diagram of a polygenic model 300 that receives input defining known genetic variants corresponding with predetermined genetic loci in an illustrative embodiment. According to FIG. 3, polygenic model 300 receives information defining known genetic variants 350 as input. Each input locus 310 at polygenic model 300 expects to receive information describing a known genetic variant (e.g., a specified nucleobase or combination of nucleobases) at a predetermined genetic locus, or a known genetic variant at a sequence of genetic loci. For example, an input locus 310 may expect information describing nucleobases occupying a contiguous sequence of predetermined genetic loci. If a known genetic variant 350 corresponding with the input locus 310 is provided, then controller 164 processes the known genetic variant when operating polygenic model 300. For example, controller 164 may apply the known genetic variants 350 as variables within genetic variant processing instructions 320, and may utilize results from prediction instructions 330 in order to make a prediction about an individual. Alternatively, if no known genetic variant 350 is provided for an input locus 310, then a value for the input locus 310 may be treated as a null or a zero, disregarded, or may be otherwise discounted.

FIG. 4 is a table 400 illustrating known genetic variants for an individual which are provided as input to a polygenic model in an illustrative embodiment. Table 400 includes multiple entries 410. Each entry 410 corresponds with one or more predetermined genetic loci, and each entry indicates a known genetic variant for the individual. Each entry 410 may also indicate whether the genetic variant is known or imputed, a genotype quality score such as a Phred quality score or a Single Nucleotide Polymorphism (SNP) score, etc. In this embodiment, an entry 410 may also include a flag stating whether genetic data has been intentionally omitted, and may further include a code stating why genetic data has been omitted. For example, the last entry 410 in table 400 has not reported SNP 3550, because the user requesting data describing this genetic locus does not have permission to access it.

Estimating Accuracy of Prediction

Each polygenic model expects to be provided a number of known genetic variants at predetermined genetic loci. However, the number of genetic variants actually provided by a user as input to a polygenic model may vary substantially. This means that even though the accuracy of a polygenic model may be well understood when all desired inputs are provided, the accuracy of the polygenic model when some data is omitted may be unknown.

The accuracy of a polygenic model will vary depending on which predetermined genetic loci remain unreported, because different genetic loci may have different levels of influence upon the polygenic model. For many polygenic models, there are a potentially limitless number of combinations of predetermined genetic loci that may remain unreported. The change in accuracy for a model when specific omissions are made is therefore hard to predict a priori, because this would involve exhaustively investigating the millions, billions, or even trillions of combinations of omissions that could occur.

Figure 5:
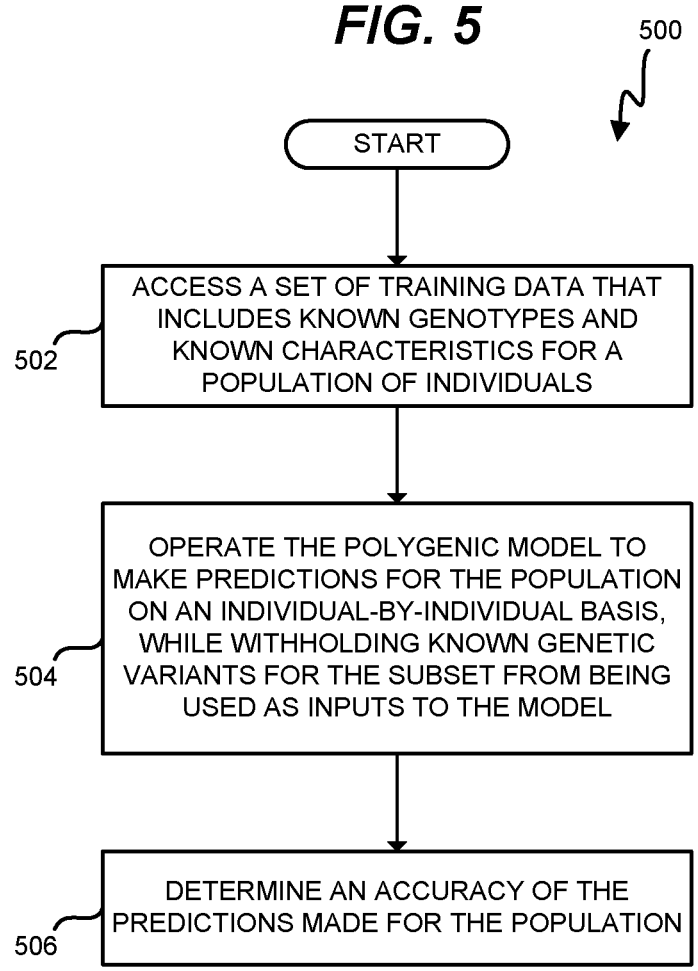
FIG. 5 is a flowchart illustrating a method for determining an accuracy of a prediction made by a polygenic model in an illustrative embodiment.

FIG. 5 is a flowchart illustrating a method 500 for determining an accuracy of a prediction made by a polygenic model in an illustrative embodiment. Assume that prior to performing method 500, controller 164 has received an indication of known genetic variants exhibited by an individual, and has operated a polygenic model to make a prediction for the individual as described in method 200. However, the indication did not provide known genetic variants for a subset of the predetermined genetic loci expected by the polygenic model. Hence, the accuracy of the prediction made by the polygenic model remains unknown. Method 500 describes a technique for determining prediction accuracy by performing a series of simulated trials on a set of training data, and may be implemented for example in step 210 of method 200.

According to method 500, in step 502 controller 164 accesses a set of training data that includes both known genotypes and known characteristics for a population of individuals. The population may be selected as a representative population of the world or portion thereof, a representative population having a similar ancestry to the individual for whom the original prediction was made, etc. Ancestry of an individual may be particularly relevant, because models that are calibrated for populations having a similar ancestry may be capable of generating predictions that are substantially more accurate and substantially more precise. The known genotypes for the set of training data may include a known genetic variant for each predetermined genetic loci used as input for the model. The characteristics known for the set of training data include characteristics that may be predicted by the polygenic model. For example, if a polygenic model makes predictions regarding the presence or absence of cardiovascular disease, the training data will include a characteristic indicating whether cardiovascular disease is actually present in each individual.

Controller 164 further operates the polygenic model to make new predictions for the population on an individual-by-individual basis in step 504. During this process, controller 164 intentionally withholds/omits providing genetic variants for the subset of predetermined genetic loci that were omitted as inputs for the original prediction. Phrased another way, the polygenic model is forced by controller 164 to consider genetic variants at the same predetermined genetic loci that were considered for the original prediction. Hence, the polygenic model may be operated with the same number and type of missing inputs as when it made its original prediction.

Controller 164 further determines an accuracy of the predictions made for the population when genetic variants for the subset have been omitted in step 506. This may comprise determining a ratio of predictions that are "hits" (i.e., accurate) to the overall number of predictions made for the population. Controller 164 may further report this ratio as an expected accuracy of the original prediction. In embodiments where characteristics are reported as numerical values, accuracy may be determined based on how close the predictions are to the numerical values. For example, controller 164 may report an average percentage of deviation or amount of deviation between predicted and actual values.

In some embodiments, controller 164 may engage in an exhaustive search of the population to determine expected accuracy for predictions made based on incomplete inputs. Alternatively, downsampling may help to reduce the processing time and/or load involved when determining expected accuracy.

Accounting for Genotype Quality

Genetic variants provided as input may be accompanied by genotype quality scores (e.g., SNP quality scores, Phred scores, etc.). Genotype quality scores do not indicate an overall health or value of a genetic variant with respect to other variants, but rather indicate a level of confidence that an individual actually has the reported genetic variant.

During sequencing of genetic material, sequencing equipment makes "calls" which report genetic variants (e.g., alleles, sequences, indels, etc.) exhibited by an individual. However, the calls are based on reads, which are individual readings of a sequence of genetic material. The number of reads (also known as "depth of sequencing") at each genetic locus may vary (e.g., between twenty and fifty reads for certain portions of the genome). Furthermore, some reads may provide data that conflicts with other reads. This means that even when there are a large number of reads, the level of confidence in the call may vary. Even a genetic locus which does not have a sufficient number of reads (or indeed, any reads) may be "imputed" as having a specific genetic variant, for example by predicting a genotype of an individual based on a population to which the individual belongs. Genotype quality scores are therefore beneficial because they indicate the amount of confidence associated with each call.

If an individual is reported as having a genetic variant with a low genotype quality score, and a prediction is made about the individual based on the existence of that genetic variant, then it may be beneficial to reduce the accuracy associated with the prediction. This is because the low genotype quality score suggests that the genetic variant might not actually be present within the individual.

Figure 6:
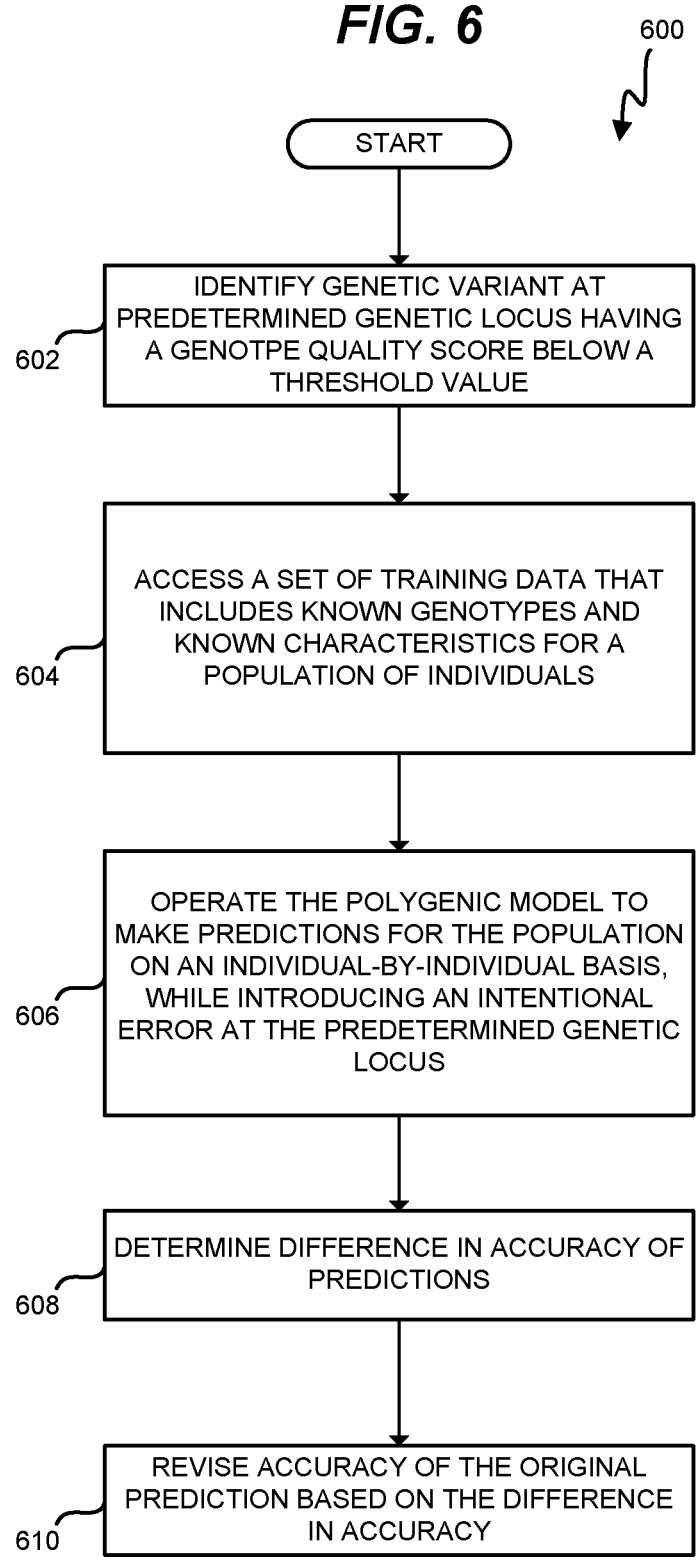
FIG. 6 is a flowchart illustrating a method for determining an accuracy of a prediction made by a polygenic model, based on genotype quality scores in an illustrative embodiment.

FIG. 6 is a flowchart illustrating a method 600 for determining an accuracy of a prediction made by a polygenic model, based on genotype quality scores in an illustrative embodiment. According to FIG. 6, in step 602 controller 164 identifies a genetic variant that occupies a predetermined genetic locus, and that has a genotype quality score below a threshold value. The threshold value may be a value indicating absolute confidence (e.g., one hundred percent confident), or may be a value indicating a lesser degree of confidence (e.g., eighty percent confident, ninety percent confidence, etc.). In embodiments where the genotype quality score takes the form of a Phred score, any suitable Phred score (e.g., one hundred, ten, one, etc.) may be used as a threshold value.

In step 604, controller 164 accesses a set of training data that includes known genotypes and known characteristics for a population of individuals. The population may also be selected as a representative population of the world or portion thereof, a representative population having a similar ancestry to the individual for whom the original prediction was made, etc. The known genotypes for the set of training data may include a known genetic variant for each predetermined genetic locus used as input for the model. The characteristics known for the set of training data include characteristics that may be predicted by the polygenic model. In one embodiment, the population exhibits the same genetic variant that the individual does at the predetermined genetic locus.

In step 606, controller 164 operates the polygenic model to make new predictions for the population on an individual-by-individual basis. As a part of this process, controller 164 introduces an intentional error at the predetermined genetic locus. That is, controller 164 intentionally alters the data provided to the predetermined genetic locus for each individual in the population, in order to introduce an input error when making the new predictions. If genetic variants were not submitted for certain genetic loci used as inputs for the polygenic model when making the original prediction, then controller 164 may withhold known genetic variants for those genetic loci when making the new predictions.

In step 608, controller 164 determines a difference in accuracy of the new predictions. For example, controller 164 may compare an aggregate accuracy of the new predictions to a known accuracy of predictions made for the population when no error has been introduced. In further embodiments, controller 164 may generate new predictions where an error is not introduced and compare the accuracy of predictions made based on an input error against the accuracy of predictions made without an input error. The difference in accuracy represents the expected amount of accuracy loss when the genetic variant for the predetermined genetic locus is misreported.

Controller 164 further determines an original accuracy of the original prediction, for example by loading a predetermined value, or by performing method 500 above. In step 610, controller 164 revises the original accuracy of the original prediction based on the difference in accuracy calculated in step 608. For example, if the difference in accuracy is five percent, and the genotype quality indicates a confidence of eighty percent in the call for the genetic variant, then the original accuracy of the original prediction may be discounted by four percent (which is eighty percent of five percent). Method 600 may be repeated for each genetic variant that is below the threshold value, in order to iteratively discount the original accuracy for each genetic variant having a genotype quality score below the threshold value.

In further embodiments, method 600 is performed upon completion of training of a polygenic model in order to determine a difference in accuracy for each predetermined genetic locus. These differences may then be combined depending on genotype quality scores associated with each predetermined genetic locus. Such a technique may be less computationally intensive, than repeating method 600 each time a new prediction is made.

Determining Changes in Proportion of Variance Explained (PVE)

In addition to or as an alternative to evaluating accuracy of a prediction, it may also be beneficial to determine changes to the PVE of a prediction made by a polygenic model, based upon the amount of genetic loci for which genetic variants are provided to the polygenic model. PVE indicates, for a given an amount of variability X in a characteristic that is attributable to inheritance, the proportion of X that is predictable by the model. Phrased another way, while heritability indicates a proportion of a trait that is genetically defined, PVE indicates an amount of the heritability that is predictable. PVE may be particularly useful in describing characteristics that fall across a range of numerical values within a population. Such characteristics include height, weight, etc.

For this embodiment, assume that a polygenic model has been operated in order to make a prediction for an individual, but that a subset of inputs have not been provided to the polygenic model. That is, no known genetic variants have been provided for a subset of predetermined genetic loci used as input for the model.

Figure 7:
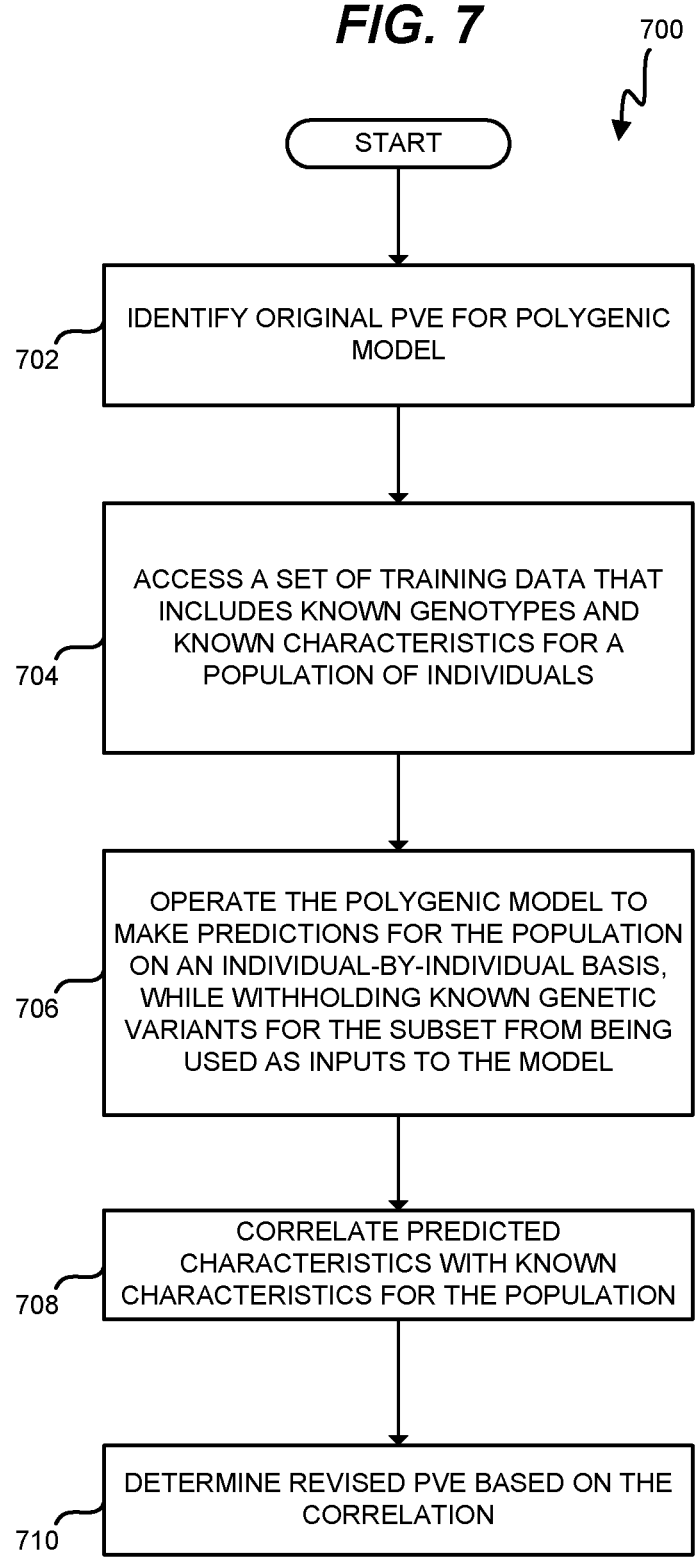
FIG. 7 is a flowchart illustrating a method for determining a Proportion of Variance Explained (PVE) of a prediction made by a polygenic model in an illustrative embodiment.

FIG. 7 is a flowchart illustrating a method 700 for determining a PVE of a prediction made by a polygenic model in an illustrative embodiment. Method 700 calculates a change in PVE for each prediction made by a polygenic model based on the inputs of the model (each corresponding with a predetermined genetic loci) that have not received a known genetic variant. In step 702, controller 164 determines an original PVE for the polygenic model. The original PVE may have been calculated by comparing known characteristics for a population described in a training set of data to predictions of those characteristics made by the polygenic model. The original PVE may for example already be stored in memory as a full or partial eta squared ($\eta^2$) value, as a full or partial omega squared ($\omega^2$) value, or may be dynamically calculated. Depending on the manner in which predictions are made and evaluated, $\eta^2$ may be equivalent to $R^2$ values found via linear regression techniques.

Figure 8:
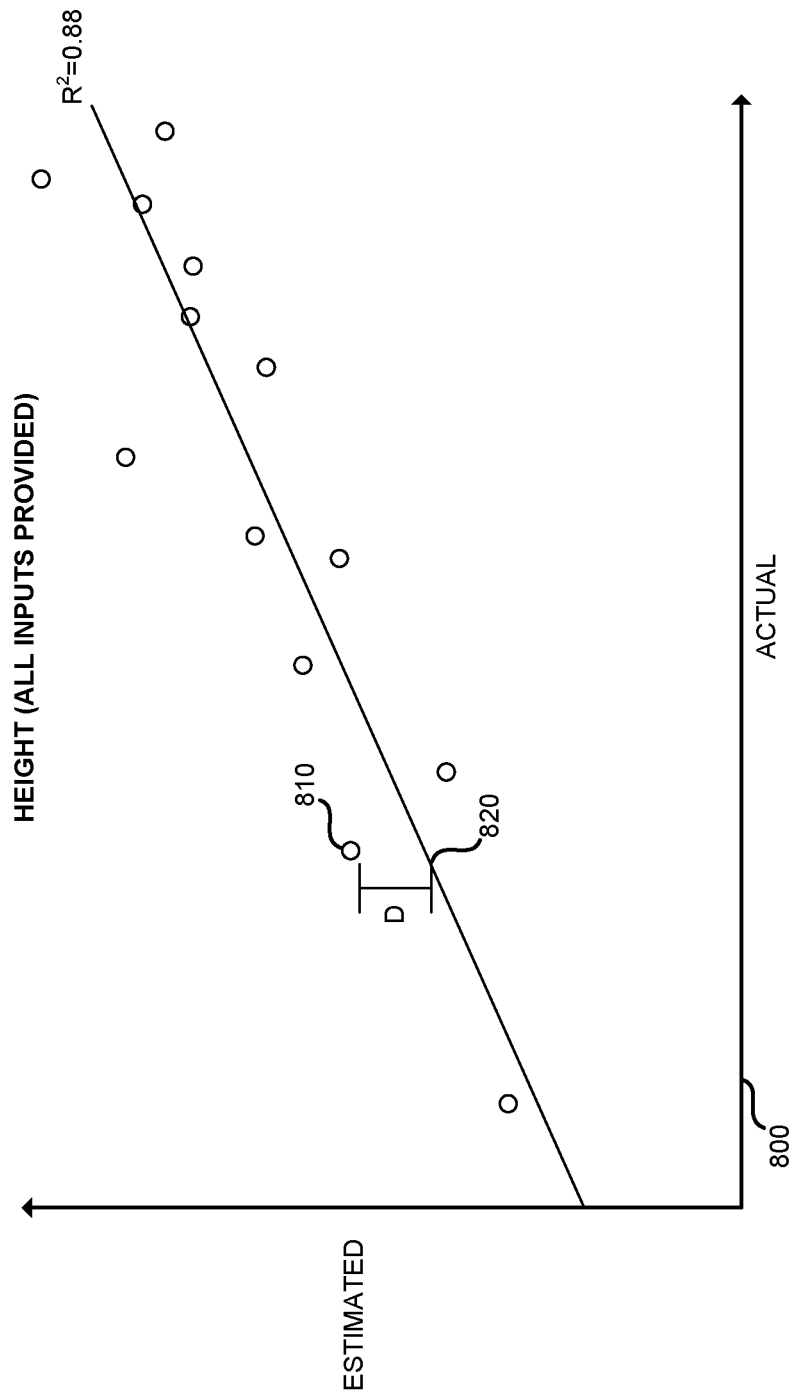
FIGS. 8-9 are charts illustrating relationships between predicted and actual values of a trait in an illustrative embodiment.

For example, an original PVE of a polygenic model that predicts height may be calculated based on chart 800 in FIG. 8. In such an example, each observed value 810 for a trait may be compared to an estimated value 820 for that trait, in order to determine deviations (D). These deviations may be squared and then summed to arrive at a Sum of Square Errors (SSE) (also referred to as a Residual Sum of Squares (RSS)) for the model. The arithmetic mean of observed values may also be calculated, and a Total Sum of Squares (TSS) may be calculated by summing the squares of differences between observations and the arithmetic mean. A PVE in the form of $\eta^2$ may then be calculated by dividing the SSE by the TSS. In embodiments where PVE is calculated in the form of $\omega^2$ (which is an unbiased value), a Mean Squared Error (MSE) may also be calculated by dividing the SSE by the number (N) of observations (e.g., the size of a population in a set of training data). Controller 164 may then determine a number of degrees of freedom (DF) in the model, and may calculate $\omega^2$ according to the following formula:

$$\omega^2 = \frac{SSE - DF(MSE)}{TSS + MSE} \quad (1)$$

In step 704, controller 164 accesses a set of training data that includes known genotypes and known characteristics for a population of individuals. The population may also be selected as a representative population of the world, a representative population having a similar ancestry to the individual for whom the original prediction was made, etc. The known genotypes for the set of training data may include a known genetic variant for each predetermined genetic loci used as input for the model. The characteristics known for the set of training data include characteristics that may be predicted by the polygenic model. In one embodiment, the population exhibits the same genetic variant as the individual does at the predetermined genetic locus.

In step 706, controller 164 predicts characteristics for the population using the model, while withholding genetic variants for the subset from being used as inputs to the polygenic model. Steps 704-706 may be performed in a similar manner to steps 502-504 of method 500 described above.

Figure 9:
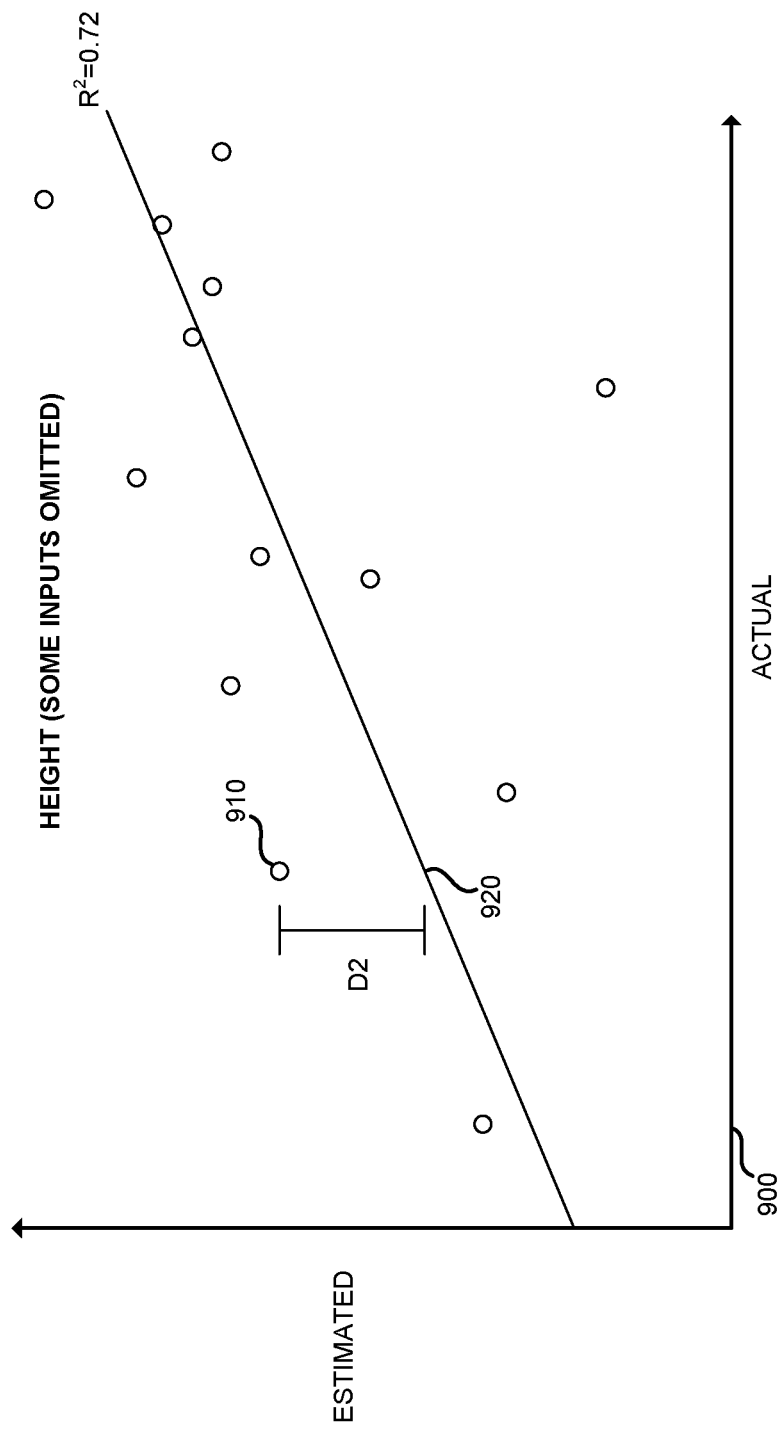

In step 708, controller 164 correlates the predicted characteristics with the known characteristics for the population. Because less information has been provided to the polygenic model in order to make the predictions, the predictions are expected to explain a lesser proportion of variance. For example, as shown in chart 900 of FIG. 9, estimated values for height vary more significantly, resulting in the model becoming unable to explain a large degree of variance in the population. Controller 164 may further calculate a new value to report as the PVE for the set of new predictions using any suitable analysis techniques. For example, each observed value 910 for a trait may be compared to an estimated value 920 for that trait, in order to determine new deviations (D2). These new deviations may be squared and then summed to arrive at an SSE for the model. The arithmetic mean of observed values may also be calculated, and a TSS may be calculated by summing the squares of differences between observations and the arithmetic mean. However, if the same population from step 702 is used, then the arithmetic mean and the TSS may already be known.

PVE in the form of $\eta^2$ may then be calculated by dividing the SSE by the TSS. In embodiments where PVE is calculated in the form of $\omega^2$, an MSE may also be calculated by dividing SSE by N. Controller 164 may then determine DF, and may calculate $\omega^2$ according to the formula (1) above.

In step 710, controller 164 determines a revised PVE for the original prediction, based on the correlation. For example, controller 164 may determine the revised PVE based on a calculated $R^2$, $\eta^2$, or $\omega^2$ value (e.g., multiplied by a scaling factor to arrive at a percentage value), or may report the revised PVE as one of these such values.

In further embodiments, an original PVE may already be known in the form of an original $\eta^2$ value. The original $\eta^2$ is equal to SSE divided by TSS, and TSS will not vary if the population used for the original and revised prediction remains the same. Thus, a new $\eta^2$ may be calculated by determining the new SSE for the training population, and dividing it by the TSS that was already determined for the original population. Alternatively, the TSS may be determined by dividing the original $\eta^2$ by the originally calculated SSE, and then may be used to calculate the new $\eta^2$.

Reporting

Figure 10:
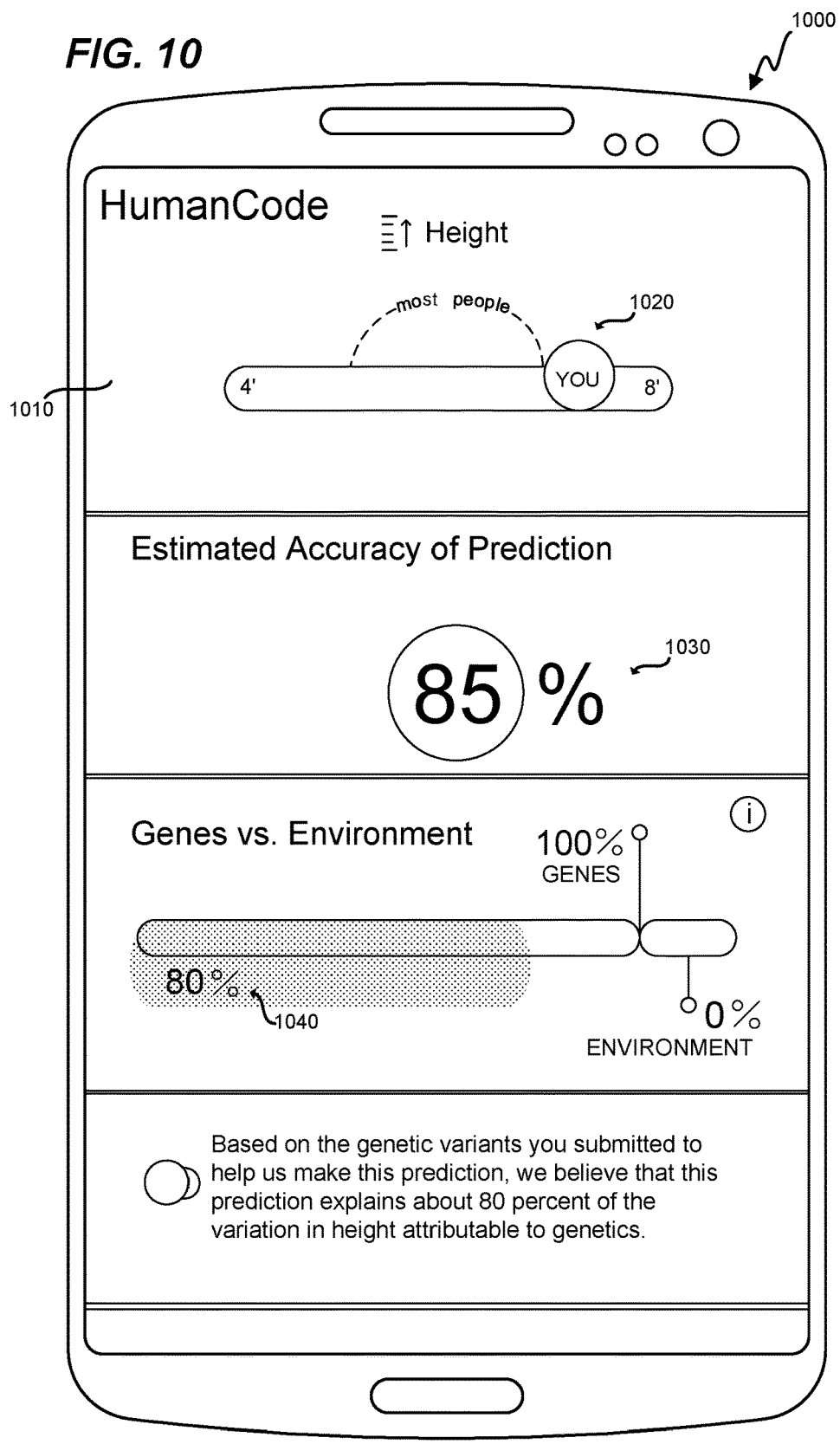
FIG. 10 is a diagram illustrating a report in an illustrative embodiment.

FIG. 10 is a diagram illustrating a report in an illustrative embodiment. The report illustrates a prediction made about a characteristic of an individual. In this embodiment, the report is provided via display 1010 (e.g., a screen) of a mobile device 1000. The report includes a graphical representation 1020 of the prediction, which in this embodiment illustrates a predicted height of an individual with respect to the general population. The graphical representation 1020 of the prediction is accompanied by a graphical representation 1030 indicating an estimated accuracy of the prediction. Additionally, the report includes a graphical representation 1040 of a PVE for the prediction.

EXAMPLES

In the following examples, additional processes, systems, and methods are described in the context of a polygenic evaluation server 160 that evaluates predictions made by polygenic models.

In this example, a user operating user device 110 sends a request to I/F 162 requesting a set of gene-based predictions relating to cardiovascular and mental characteristics, based on the user's genetic data. The user indicates that the results should be sent to third party server 130, which in this instance is a server of a medical organization. Controller 164 determines that polygenic models 174 and 176 will be used to make the requested predictions. Polygenic model 174 utilizes seven hundred predetermined genetic loci as inputs across seven chromosomes, while polygenic model 176 utilizes twelve thousand predetermined genetic loci across nineteen chromosomes.

Controller 164 operates I/F 162 to generate a request to for genetic variants at the predetermined genetic loci used by models 174 and 176. Genomics server 120 responds with an indication (e.g., an electronic record) reporting known genetic variants for most, but not all, of the predetermined genetic loci. Certain genetic variants are not reported because they have not been genotyped or sequenced, while others are not reported because permission has not been granted by the user to share this data. This may be because the user does not wish to share this data when making the current set of predictions, does not wish third party server 130 to receive information based on this data, etc.

Controller 164 further operates polygenic models 174 and 176 to make predictions for the individual, by using known genetic variants at the predetermined genetic loci as inputs to the polygenic models. The polygenic models then make predictions regarding the cardiovascular and mental characteristics of the user.

The accuracy and PVE of these predictions are at this time unknown, and hence the usefulness of the predictions is unknown. In order to address these issues, controller 164 accesses a set of training data for a population having the same sex as the user and has shared ancestors with the user. Individuals in the population have known cardiovascular and mental characteristics, and also have known genotypes. Controller 164 acquires a sample of one thousand individuals from the population, and makes new predictions for these individuals by submitting genetic variants to the predictive models for the exact same set of predetermined genetic loci that had known genetic variants for the user. For each predicted characteristic, controller 164 determines a ratio of accurate to inaccurate predictions for the new predictions, transforms the ratio into a percentage, and reports the percentage as an estimated accuracy of the originally predicted characteristic for the user. The new predictions made for the population are then discarded.

For characteristics that are numerical, controller 164 compares estimated to actual values. Controller 164 also calculates a PVE for each characteristic based on comparisons of estimated to actual values. Controller 164 proceeds to generate a report indicating each predicted characteristic for the user, as well as an estimated accuracy and PVE for each predicted characteristic, and operates I/F 162 to transmit the report to third party server 130 as well as user device 110.

Figure 11:
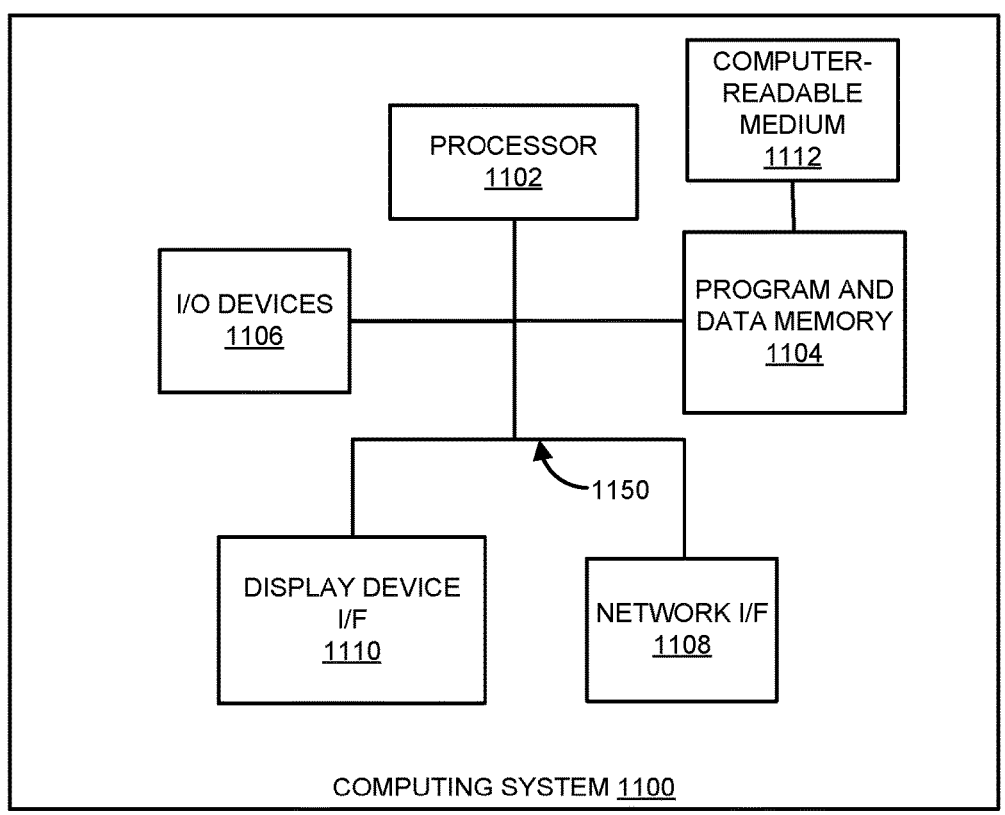
FIG. 11 depicts an illustrative computing system operable to execute programmed instructions embodied on a computer readable medium.

Embodiments disclosed herein can take the form of a hardware processor implementing programmed instructions, as hardware, as firmware operating on electronic circuitry, or various combinations thereof. In one particular embodiment, instructions stored on a computer readable medium are used to direct a computing system of user device 110, polygenic evaluation server 160 and/or notification server 140 to perform the various operations disclosed herein. FIG. 11 illustrates an illustrative computing system 1100 operable to execute a computer readable medium embodying programmed instructions. Computing system 1100 is operable to perform the above operations by executing programmed instructions tangibly embodied on computer readable storage medium 1112. In this regard, embodiments of the invention can take the form of instructions (e.g., code) accessible via computer-readable medium 1112 for use by computing system 1100 or any other instruction execution system. For the purposes of this description, computer readable storage medium 1112 comprises any physical medium that is capable of storing the program for use by computing system 1100. For example, computer-readable storage medium 1112 may be an electronic, magnetic, optical, electromagnetic, infrared, semiconductor device, or other non-transitory medium. Examples of computer-readable storage medium 1112 include a solid state memory, a magnetic tape, a removable computer diskette, a random access memory (RAM), a read-only memory (ROM), a rigid magnetic disk, and an optical disk. Current examples of optical disks include compact disk—read only memory (CD-ROM), compact disk—read/write (CD-R/W), and DVD.

Computing system 1100, which stores and/or executes the instructions, includes at least one processor 1102 coupled to program and data memory 1104 through a system bus 1150. Program and data memory 1104 include local memory employed during actual execution of the program code, bulk storage, and/or cache memories that provide temporary storage of at least some program code and/or data in order to reduce the number of times the code and/or data are retrieved from bulk storage (e.g., a spinning disk hard drive) during execution.

Input/output or I/O devices 1106 (including but not limited to keyboards, displays, pointing devices, etc.) may be coupled either directly or through intervening I/O controllers. Network adapter interfaces 1108 may also be integrated with the system to enable computing system 1100 to become coupled to other data computing systems or storage devices through intervening private or public networks. Network adapter interfaces 1108 may be implemented as modems, cable modems, Small Computer System Interface (SCSI) devices, Fibre Channel devices, Ethernet cards, wireless adapters, etc. Display device interface 1110 may be integrated with the system to interface to one or more display devices, such as screens for presentation of data generated by processor 1102.

What is claimed is:

1. A system comprising:
a memory storing a polygenic model in the form of a neural network that uses genetic variants which occupy predetermined genetic loci as inputs;
an interface that receives an indication of genetic variants known to be exhibited by an individual; and
a controller that operates the neural network to make a prediction for the individual based on the indication, determines that the indication does not provide genetic variants for a subset of the predetermined genetic loci, and evaluates a performance of the prediction of the neural network by operating the neural network to make additional predictions for additional individuals, wherein the additional predictions are produced by withholding genetic variants for the subset, while also including genetic loci referred to by the indication.

2. The system of claim 1 wherein:
the controller evaluates the performance of the neural network as an estimated accuracy of the prediction made by the neural network for the individual.

3. The system of claim 2 wherein:
the controller determines the estimated accuracy of the prediction by accessing a set of training data that includes genotypes and characteristics known for a population of individuals, operating the neural network to make new predictions for the population on an individual-by-individual basis, while withholding genetic variants for the subset of the predetermined genetic loci from being used as inputs to the neural network, and determining an accuracy of the new predictions.

4. The system of claim 2 wherein:
the controller determines a genotype quality for at least one of the genetic variants, and the controller calculates the estimated accuracy based on the genotype quality.

5. The system of claim 1 wherein:
the controller evaluates the performance of the neural network as a Proportion of Variance Explained (PVE) for the prediction.

6. The system of claim 5 wherein:
the controller determines the PVE for the prediction by accessing a set of training data that includes genotypes and characteristics known for a population of individuals, operating the neural network to make new predictions for the population on an individual-by-individual basis, while withholding genetic variants for the subset of the predetermined genetic loci from being used as inputs to the neural network, and determining a PVE of the new predictions.

7. The system of claim 1 wherein:
the predetermined genetic loci comprise at least ten genetic loci, and the additional individuals comprise at least fifty individuals.

8. A method comprising:
selecting a polygenic model in the form of a neural network that uses genetic variants which occupy predetermined genetic loci as inputs;
receiving an indication of genetic variants known to be exhibited by an individual;
operating the neural network to make a prediction for the individual based on the indication;
determining that the indication does not provide genetic variants for a subset of the predetermined genetic loci; and
evaluating a performance of the prediction of the neural network by operating the neural network to make additional predictions for additional individuals, wherein the additional predictions are produced by withholding genetic variants for the subset, while also including genetic loci referred to by the indication.

9. The method of claim 8 wherein:
evaluating the performance of the neural network comprises determining an estimated accuracy of the prediction made by the neural network for the individual.

10. The method of claim 9 wherein:
determining the estimated accuracy of the prediction comprises:
accessing a set of training data that includes genotypes and characteristics known for a population of individuals;
operating the neural network to make new predictions for the population on an individual-by-individual basis, while withholding genetic variants for the subset of the predetermined genetic loci from being used as inputs to the neural network; and
determining an accuracy of the new predictions.

11. The method of claim 9 further comprising:
determining a genotype quality for at least one of the genetic variants; and
calculating the estimated accuracy based on the genotype quality.

12. The method of claim 8 wherein:
evaluating the performance of the neural network comprises determining a Proportion of Variance Explained (PVE) for the prediction.

13. The method of claim 12 wherein:
determining the PVE for the prediction comprises:
accessing a set of training data that includes genotypes and characteristics known for a population of individuals;
operating the neural network to make new predictions for the population on an individual-by-individual basis, while withholding genetic variants for the subset of the predetermined genetic loci from being used as inputs to the neural network; and
determining the PVE of the new predictions.

14. The method of claim 8 wherein:
the predetermined genetic loci comprise at least ten genetic loci, and the additional individuals comprise at least fifty individuals.

15. A non-transitory computer readable medium embodying programmed instructions which, when executed by a processor, are operable for performing a method comprising:
selecting a polygenic model in the form of a neural network that uses genetic variants which occupy predetermined genetic loci as inputs;
receiving an indication of genetic variants known to be exhibited by an individual;
operating the neural network to make a prediction for the individual based on the indication;
determining that the indication does not provide genetic variants for a subset of the predetermined genetic loci; and
evaluating a performance of the prediction of the neural network by operating the neural network to make additional predictions for additional individuals, wherein the additional predictions are produced by withholding genetic variants for the subset, while also including genetic loci referred to by the indication.

16. The medium of claim 15 wherein:
evaluating the performance of the neural network comprises determining an estimated accuracy of the prediction made by the neural network for the individual.

17. The medium of claim 16 wherein:
determining the estimated accuracy of the prediction comprises:
- accessing a set of training data that includes genotypes and characteristics known for a population of individuals;
- operating the neural network to make new predictions for the population on an individual-by-individual basis, while withholding genetic variants for the subset of the predetermined genetic loci from being used as inputs to the neural network; and
- determining an accuracy of the new predictions.

18. The medium of claim 16 wherein the method further comprises:
- determining a genotype quality for at least one of the genetic variants; and
- calculating the estimated accuracy based on the genotype quality.

19. The medium of claim 15 wherein:
evaluating the performance of the neural network comprises determining a Proportion of Variance Explained (PVE) for the prediction.

20. The medium of claim 19 wherein:
determining the PVE for the prediction comprises:
- accessing a set of training data that includes genotypes and characteristics known for a population of individuals;
- operating the neural network to make new predictions for the population on an individual-by-individual basis, while withholding genetic variants for the subset of the predetermined genetic loci from being used as inputs to the neural network; and
- determining the PVE of the new predictions.

* * * * *